United States Patent [19]

Snead

[11] Patent Number: 4,669,979
[45] Date of Patent: Jun. 2, 1987

[54] ORTHODONTIC PLIER
[75] Inventor: Wilford A. Snead, Glendora, Calif.
[73] Assignee: Unitek Corporation, Monrovia, Calif.
[21] Appl. No.: 806,709
[22] Filed: Dec. 9, 1985
[51] Int. Cl.⁴ .............................................. A61C 7/00
[52] U.S. Cl. ...................................................... 433/4
[58] Field of Search ........................ 433/4, 159, 160, 3
[56] References Cited

U.S. PATENT DOCUMENTS

| | | |
|---|---|---|
| 414,311 | 11/1889 | Haussmann . |
| 566,608 | 8/1896 | McLean . |
| 984,756 | 2/1911 | Frisch . |
| 1,385,481 | 7/1921 | Williams .............................. 433/159 |
| 1,594,143 | 7/1926 | Angle et al. . |
| 2,660,786 | 12/1953 | Loyd ...................................... 30/182 |
| 2,985,962 | 5/1961 | Shiner ..................................... 32/66 |
| 3,986,265 | 10/1976 | Cusato ..................................... 32/66 |
| 4,201,213 | 5/1980 | Townsend ........................... 128/312 |

Primary Examiner—Robert Peshock
Attorney, Agent, or Firm—Christie, Parker & Hale

[57] ABSTRACT

An orthodontic plier with opposed jaw portions that can be moved toward one another in a substantially straight-line motion to pry a removable cap off a convertible buccal tube without exerting a twisting force on the tooth and without an exposed tip that can slip and damage soft mouth tissue is disclosed. One jaw portion has a pointed tip that can be inserted into one end of the buccal tube and the other jaw portion has a flat surface for bracing the other end of the buccal tube and a notch therein for receiving the pointed tip of the other jaw portion.

12 Claims, 8 Drawing Figures

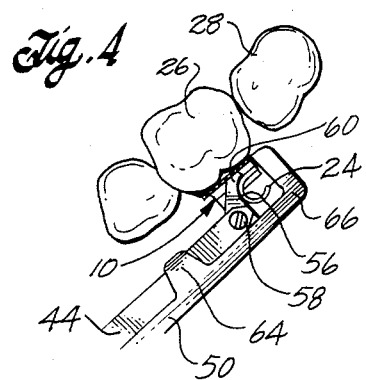
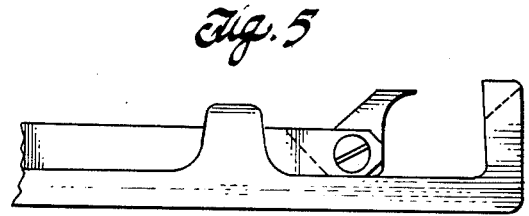
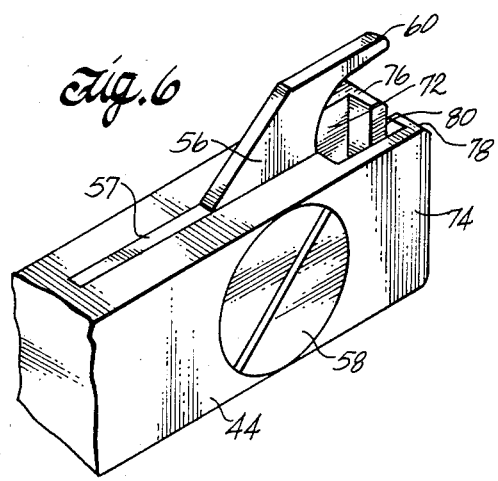
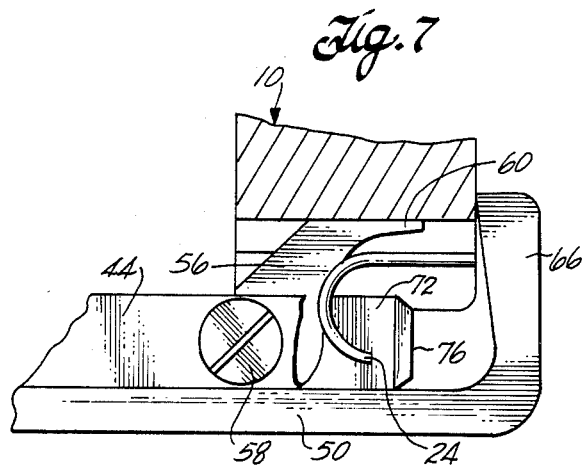

ORTHODONTIC PLIER

BACKGROUND OF THE INVENTION

Orthodontic treatment of improperly positioned teeth involves the application of mechanical forces to urge the teeth into correct alignment and orientation. The most common form of treatment involves use of orthodontic brackets which are small slotted bodies configured for direct attachment to the labial and buccal (facing the lips and cheeks) or lingual (facing the tongue) surfaces of the teeth, or alternatively for attachment to bands which are in turn cemented or otherwise secured around the teeth. A resilient curved arch wire is then seated in the bracket slots, and the arch wire is bent or twisted before installation whereby the restoring force exerted by the seated resilient wire tends to shift the teeth into orthodontically correct alignment. Depending on the shape of the arch wire (both round and rectangular cross-sections are in common use) and the orientation of the bracket slot, it is possible to apply forces which will shift, rotate or tip the teeth in any desired direction.

Conventional orthodontic brackets include tie wings around which small ligature wires are tied to hold the arch wire in a securely seated position in the brackets. Ligatures or some other form of fastening means are essential to insure that the activated arch wire is properly positioned around the dental arch, and to prevent the wire from being dislodged from the bracket slots during chewing of food, brushing of the teeth, or application of other forces to the wire by the patient. In addition, the arch wire is anchored at either end by brackets having tubes rather than slots therein and attached to the teeth at the opposite ends of the dental arch. These teeth, normally molars, are used to anchor the arch wire because they have the strongest root structure.

When, as is often the case, orthodontic treatment is begun when the patient is relatively young, the second molars will not yet have erupted and the arch wire will be anchored on the first molars. After the second molars come in, normally around age twelve, an orthodontist will usually want to attach a new arch wire anchored on these second molars with their stronger root structure. Because of the bends or twists in the arch wire and the varying orientations of the brackets, it would be difficult, if not impossible, for the orthodontist to thread the new arch wire through tubes in the first-molar brackets into tubes in the second-molar brackets for anchoring. Therefore, the tube in a bracket to be placed on a first molar will have a removable or severable cap, and the bracket will have tie wings enabling conversion into a slotted bracket. This allows the orthodontist to anchor the new arch wire on the second molars without removing and replacing the brackets originally attached to the first molars.

Currently, the removable cap is pried off using a cap removal tool consisting of a blade having a pointed L-shaped tip mounted on a standard scalpel handle. The tip of this tool is inserted into the end of the tube and the handle rotated away from the bracket so the tool tip presses upward against the inside surface of the cap and peels the cap off. This removal technique is unsatisfactory because it exerts a twisting or torquing force on the tooth that causes discomfort to the patient and could damage the tooth, and because the tool could slip during the prying process and injure the patient's cheek with its sharp point.

The present invention overcomes these problems by providing an orthodontic plier with opposed jaw portions that act to pry a removable cap off without exerting a twisting force on the tooth, and without an exposed tip that can damage soft mouth tissue. One jaw portion has a pointed L-shaped tip and the other a flat surface with a slot therein for receiving the L-shaped tip of the other jaw portion. The plier is configured so that the jaw portions can be moved toward one another in a substantially straight-line fashion once the tip has been inserted in a bracket tube. Thus a peeling action is exerted on the removable cap without a twisting action being exerted on the tooth to which the bracket is attached.

SUMMARY OF THE INVENTION

In general terms, the present invention involves a method or apparatus for removing a convertible buccal tube cap wherein one end of the convertible buccal tube is braced, a prying tip is inserted into the opening at the other end of the convertible buccal tube and then the prying tip is moved toward the braced end of the convertible buccal tube so as to effect an upward shearing force on the cap of the convertible buccal tube. This upward shearing force is absorbed by the apparatus itself and is not transmitted to the tooth on which the convertible buccal tube is mounted.

More specifically, the present invention involves an orthodontic plier apparatus having a first arm, a second arm pivotally connected to the first arm between their ends, a prying jaw means operatively connected to one end of the first arm, and an anvil jaw means connected to one end of the second arm so as to be opposed to the prying jaw means. The plier is adapted so that upon pivoting of the ends of the arms toward one another the jaw means can move toward one another in a straight-line fashion. The anvil jaw means can brace one end of a convertible buccal tube and the prying jaw means provides a prying tip for insertion into the opening at the other end of the convertible buccal tube, permitting removal of a convertible buccal tube cap without imposing potentially damaging forces on the associated tooth.

In addition, the connection of the prying jaw means to one end of the first arm can involve a slider bar means extending therebetween. In this case the anvil jaw means is connected to one end of the second arm by a support bar means extending therebetween and positioned so that the slider bar means can slide over its upper surface during pivoting of the ends of the arms with respect to one another. By adjusting the length of the slider bar means and the support bar means, an offset can be introduced into the plier to enhance its ability to be used inside a patient's mouth at the distal ends of the dental arch.

It is also preferable to provide the plier with guide means restraining the slider bar means to straight-line sliding motion over the support bar means during pivoting of the ends of the arms with respect to one another at at least two points along the length of the slider bar means. Having the prying jaw means or a prying tip removably attached is also desirable so that it can be replaced when worn.

BRIEF DESCRIPTION OF THE DRAWINGS

FIG. 4 is an occlusal view of a portion of the dental arch with the jaw portions of the orthodontic plier peeling a removable cap from an orthodontic bracket;

FIG. 5 is a side view of the jaw portions of the orthodontic plier;

FIG. 6 is a perspective view of an alternate embodiment for one jaw portion of the orthodontic plier; and FIG. 7 is a side view (partly broken away) of the jaw portions of the plier shown in FIG. 7, and in the process of peeling a removable cap from an orthodontic bracket.

DESCRIPTION OF THE PREFERRED EMBODIMENT

Although orthodontic treatment can be performed using brackets attached to the lingual surfaces of the teeth and the orthodontic plier according to the present invention could be used in connection with such treatment, it is more common to attach the brackets to the labial and buccal surfaces of the teeth in younger patients and the preferred embodiment will therefore be described in connection with this type of treatment.

Figure 1:
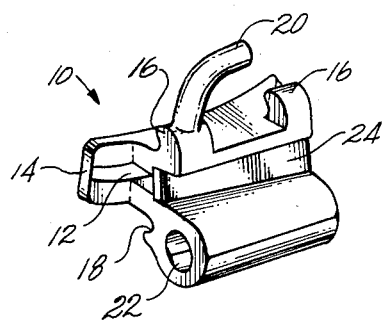
FIG. 1 is a perspective view of an orthodontic bracket with a tube having a removable cap of the type removed by an orthodontic plier according to the present invention.

With reference to FIG. 1, an orthodontic bracket 10 commonly called a buccal tube is depicted having a rectangular cross-section tube 12 extending through it mesiodistally (lengthwise along the dental arch) for receiving a rectangular cross-section arch wire. The bracket depicted is intended to be a typical one which might be attached to the buccal surface of an upper molar. An arcuate base 14 provides a surface whereby the bracket can be bonded directly to the tooth or to a tooth band. Tie wings 16 extending gingivally (toward the gum) and tie wing undercut 18 extending occlusally (toward the biting surface of the tooth) provide anchor extensions around which ligature wires or a comparable fastening means can be tied.

The bracket on the anchor tooth may also carry additional orthodontic fixtures. A hook 20 extends gingivally and then distally (toward an end point of the dental arch) from one of the tie wings to provide an anchor for an intraoral force exerting element such as a spring or elastic band. An occlusal headgear tube 22 with a circular cross-section extends mesiodistally through the bracket for receiving one of the distal ends of the intraoral portion of a facebow connected to extraoral force exerting head straps.

Orthodontic brackets can be constructed from any material that is compatible with the environment of the mouth; plastic or stainless steel being examples of two such materials. Buccal tubes are ordinarily constructed of stainless steel for strength. Bracket 10 is cast in one piece except for a removable cap 24 which is brazed into place on the bracket to form the buccal wall of tube 12. Cap 24 can be peeled off at the brazing to convert tube 12 into a mesiodistally extending slot. An arch wire can then be lowered into this slot and ligature wires wrapped around bracket 10 under tie wings 16 and tie wing undercut 18 to hold the arch wire securely in place in the bracket.

Figure 3A:
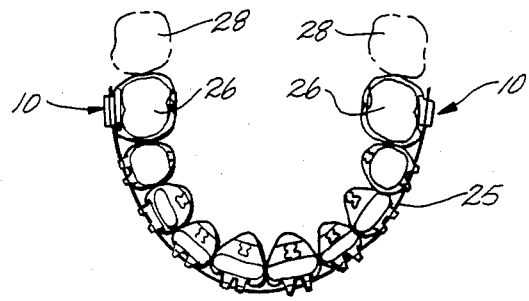
FIG. 3A is an occlusal view of an upper dental arch with an arch wire mounted in orthodontic brackets attached to the labial and buccal surfaces of the teeth and terminating on the first molars.
Figure 3B:
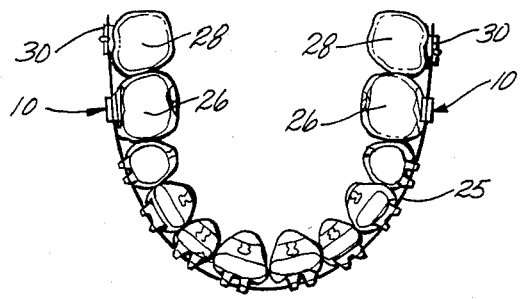
FIG. 3B is an occlusal view of a dental arch as shown in FIG. 3A with the arch wire terminating on the second molars.

With reference to the sequence of FIG. 3A to FIG. 3B, a situation is depicted where use of a convertible buccal tube like bracket 10 is desirable. In FIG. 3A, an arch wire 25 has been terminated at each end of the dental arch on the first molars 26. Eventually, when second molars 28 come in, the orthodontist would like to insert an arch wire that is terminated at each end of the dental arch on the second molars, as shown in FIG. 3B. With this eventuality in mind, and to reduce the time and trouble involved in inserting a new arch wire, the orthodontist will anchor the distal ends of the first arch wire on the first molars in a convertible buccal tube like bracket 10. Then, when it comes time to anchor the distal ends of a new arch wire in a pair of conventional buccal tubes 30, removable caps 24 can be peeled from brackets 10 to allow them to be used like any other conventional slotted orthodontic bracket. This obviates the need for replacing brackets 10 with such conventional brackets.

Figure 2:
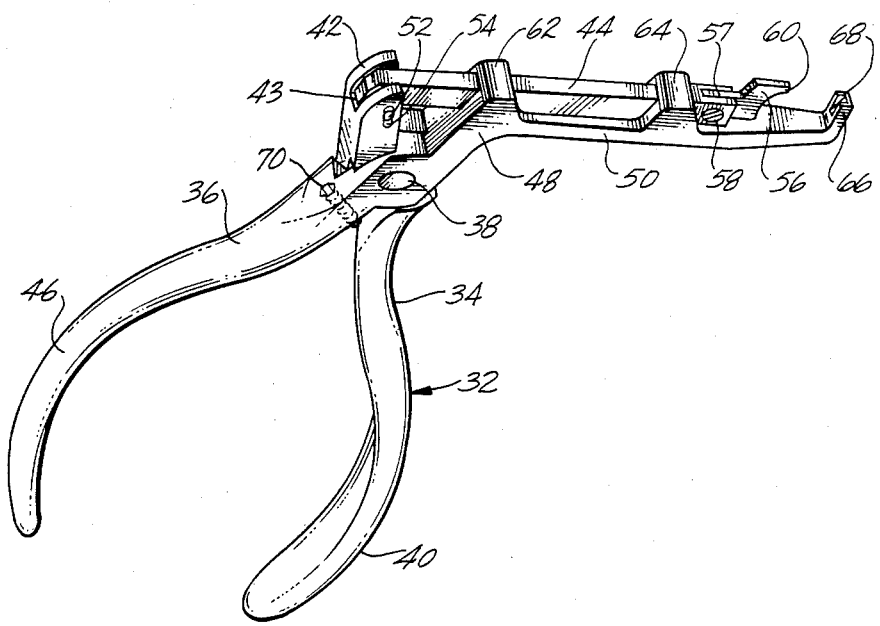
FIG. 2 is a perspective view of an orthodontic plier according to the present invention.

The remaining difficulty to be overcome is finding a way to remove the cap safely and efficiently from the convertible buccal tube. With reference to FIG. 2, an orthodontic plier 32 according to the present invention provides for the desired safe and efficient cap removal. Plier 32 includes a pair of conventional plier arms 34 and 36 which are pivotally connected by a hinge-pin bolt 38. Arm 34 terminates at one end in a handle 40 and at the other end in a tip portion 42. This tip portion has a U-shaped slot 43 in which a slider bar 44 is mounted. Arm 36 terminates at one end in a handle 46 opposite handle 40, and at the other end in a tip portion 48 opposite tip portion 42. Tip portion 48 has a support bar 50 mounted on it. Slider and support bars 44 and 50 extend laterally (and preferably about perpendicularly) from an imaginary plane positioned centrally between fully opened handles 40 and 46 and extending through and parallel to the axis of hinge-pin bolt 38.

Slider bar 44 is an elongated member with a rectangular cross section that is rotatably mounted at one end in slot 43 and extends out toward opposing tip portion 48. The slider bar is mounted in slot 43 by a cylindrical pin 52 which extends through one end of the slider bar and is received at opposite ends in elongated apertures 54 in the opposed walls of slot 43. Apertures 54 are elongated to allow some play in the mounting during manipulation of the plier. The elongation is along the length of arm 34. This type of mounting allows slider bar 44 to rotate in the angle which it assumes with respect to arm 34, and to change the position of pin 52 along the length of arm 34 as required during movement of the plier arms about bolt 38 with respect to one another.

At the other end of slider bar 44, a peeling or prying tip 56 is attached which forms one of the jaw portions of the orthodontic plier. Peeling tip 56 is roughly an inverted L-shaped thin piece mounted in the plane of the plier arms in a slot 57 cut into the end of the slider bar. A screw 58 extending through the end of the slider bar orthogonal to the plane of tip 56 effects the attachment of the tip to the slider bar. The head of screw 58 can be adapted to allow it to be unscrewed by conventional slot-head or Phillips-head screw drivers or by a conventional Allen wrench. A head adapted for a slot-head screw driver is depicted in the preferred embodiment, as this type of screw driver is most readily available. A removable screw is used to attach tip 56 so it can be replaced with a new tip as the old tip becomes worn from use.

A detailed side view of tip 56 is shown in FIG. 5. The upper member of the inverted L-shaped tip extends out and away from the end of slider bar 44. It has an uppper surface which is flat and a lower surface which curves into the side member of the L-shaped tip so that the thickness of the tip increases away from a remote point 60. The dimensions of this remote point of tip 56 should be such that it can fit into the end of tube 12. The tip extends above the upper surface of the slider bar so that it is clearly visible from behind enabling an orthodontist to guide it into the end of tube 12 while looking into a patient's mouth.

The bottom surface of slot 57 is slanted with respect to the end of the slider bar so that the slot is deeper near the upper surface of the slider bar. The back side of the side member of tip 56 opposite the remote point is also slanted to match slot 57. When point 60 is acting on tube 12, tip 56 will tend to rotate about screw 58. The slanted surface of slot 57 provides a greater surface along which the surface of the tip can press to resist this tendency. This allows the tip to last longer before needing replacing, and ensures that the tip will not twist during cap removal and transmit a twisting force to the tooth.

Support bar 50 is a flat rectangular and elongated piece which is fixedly attached (and preferably integrally formed) at one end to tip portion 48 and extends out from tip portion 48 at an angle slightly greater than 90° with the rest of arm 36 in a direction away from tip portion 42. The support bar is positioned so that slider bar 44 can rest upon and slide along its upper surface 35 longitudinally. Support bar 50 is wider than slider bar 44 so that it extends out beyond the sides of the slider bar on either side. To hold the slider bar next to the support bar so that the two will slide together in a straight-line fashion, a pair of bridges 62 and 64 are provided along the length of the support bar. These bridges extend up from the support bar on opposite sides of the slider bar and pass over the slider bar to form guides through which the slider bar can move. The bridges are preferably spaced apart from one another to prevent the two bars from moving in a nonparallel manner with respect to one another. To this end, bridge 62 is positoned at tip portion 48 and bridge 64 is positioned toward the jaw portions of the pliers as close as it can be without interfering with the operation of the jaw portions.

The remote end of support bar 50 extends out beyond the remote end of slider bar 44 and then turns upward at roughly 90° to provide a flat anvil 66 opposite tip 56 that is the other jaw portion of the plier. The face of anvil 66 opposite tip 56 has a notch 68 at its top end which receives the tip when the plier is closed. Point 60 slides into this notch to protect a patient's cheek from injury and to ensure that the cap can be completely peeled off if desired. The lengths of the slider bar and support bar are such that point 60 rests in notch 68 when the plier is closed and is far enough away from the notch when the plier is open to allow positioning of the jaw portions of the plier on opposite sides of the buccal tube.

Although the preferred embodiment has been described with tip 56 mounted on the jaw portion attached to the slider bar and anvil 66 mounted on the jaw portion attached to the support bar, it would be apparent to a person skilled in the art that alternate jaw arrangements or configurations could be used without departing from the teachings of the present invention. For example, an anvil could be mounted on the slider bar to oppose a tip mounted on the support bar. Alternatively, a tip could be mounted on the slider bar to oppose a tip mounted on the support bar. This last arrangement would not allow the cap to be completely peeled off, but this may be desirable for reasons discussed below.

With reference to FIG. 4, the jaw portions of the orthodontic plier according to the presently preferred embodiment of the invention are shown in operation. With the plier in the open position with handles 40 and 46 pivoted apart from one another, anvil 66 is placed against the distal side of bracket 10. Handles 40 and 46 are then pivoted toward one another while care is taken that point 60 moves into the mesial end of tube 12. The handles are further pivoted toward one another so that tip 56 continues to move in a straight line toward anvil 66. The curved lower surface of tip 56 contacts cap 24 and begins peeling it up and curling it back as shown in FIG. 4. Although cap 24 can be completely peeled off, it is presently thought that it is best to leave the cap just barely attached to the bracket if possible and then use a conventional needle nose plier to complete the detachment and retrieve the cap. Otherwise, the cap may fall down between the cheek and gum where it is awkward to retrieve.

A set screw 70, threadably received in plier arm 36 adjacent hinge-pin bolt 38 in handle portion 46, provides a way of adjusting the extent to which a cap is removed. To preset the plier for partial removal of the cap, the setscrew can be turned clockwise with an Allen wrench with the plier handles closed until the slide bar tip retracts from the notch in anvil 66. Leaving a gap of 0.005 inch between the tip and the notch will result in approximately 80% cap removal on most buccal tubes when the plier is used. This setting can be tested on a buccal tube from inventory and fine-tuned until a desired amount of cap removal is achieved. If a jaw arrangement with two opposed tips is used, the setscrew can be adjusted to prevent the tips from contacting one another and thereby prevent the two tips from damaging one another.

Alternatively, a cap retention means can be provided for the orthodontic plier so that upon complete cap removal the cap is retained with the plier for removal from the patient's mouth. An alternate embodiment of the present invention including such a cap retention means is shown in FIGS. 6 and 7. The cap retention means comprises a pair of side walls 72 and 74 which extend out from either side of the end of the slider bar where tip 56 is mounted. At the opposed, remote ends of these side walls a pair of end walls 76 and 78 are attached and extend toward one another leaving only a narrow slit 80 between them. Slit 80 is present to allow slot 57 to be cut into the end of the slider bar during manufacture of the orthodontic plier and should not be wide enough for cap 24 to fit through.

With reference to FIG. 7, the cap retention means is shown in operation. With support bar 50 acting as a bottom surface, the cap retention means forms a well into which the cap goes during removal. Upon complete removal, the coaction of tip 56 and the cap retention means hold cap 24 in place so that it can be removed from the patient's mouth. To avoid any possibility of the cap falling out of the cap retention means the plier should be rotated by the orthodontist to a position where gravity will act to hold the cap in place before the plier is brought out of the patient's mouth.

The arms, slider bar and support bar of the plier are preferably constructed of 17-4 PH stainless steel. Pin 52 is made of 302 or 304 stainless steel and tip 56 and screw 58 of 420 stainless steel. The tip is to be hardened to Rockwell 50 RC to provide longer life. The gap between point 60 and anvil 66 should be about 0.25 to 0.30 inch when the plier is in the open position to accommodate presently available convertible buccal tubes. Point 60 would extend into notch 68 about 0.025 inch to ensure that the cap can be completely sheared off when the plier is closed.

The plier described above overcomes the problems associated with prior methods of removing caps brazed onto convertible buccal tubes. The forces generated by cap removal are absorbed by the plier itself so no damaging forces are transmitted to the tooth and the prying tip cannot slip and damage a patient's cheek. As described above, the jaw portions of the plier are offset. While this offset is not critical to the operation of the plier, it is a preferred feature because the convertible buccal tubes are located at the distal ends of the dental arch. The offset, therefore, allows for easier manipulation of the plier handles outside of the patient's mouth while the jaw portions operate inside the mouth.

What is claimed is:

1. A plier apparatus comprising:
   a first arm;
   a second arm pivotally connected to the first arm between their ends;
   a slider bar means operatively connected at one end to one end of the first arm;
   a prying jaw means, having a remote point capable of being inserted into the end of a buccal tube and a thickness that increases away from the remote point, attached to the other end of the slider bar means;
   a support bar means connected at one end to one end of the second arm and positioned so that the slider bar means can slide over its upper surface during pivoting of the ends of the arms with respect to one another; and
   an anvil jaw means connected to the other end of the support bar means so as to be opposed to the prying jaw means such that upon pivoting of the ends of the arms toward one another the jaw means move toward one another in a straight-line fashion.

2. A plier apparatus according to claim 1 also comprising guide means restraining the slider bar means to straight-line sliding motion over the support bar means during pivoting of the ends of the arms with respect to one another at at least two points along the length of the slider bar means.

3. A plier apparatus according to claim 1 wherein the prying jaw means is removably attached to the other end of the slider bar means so that it can be replaced when worn.

4. An orthodontic plier apparatus comprising a first arm;
   a second arm pivtally connected to the first arm between their ends;
   a second jaw means connected to one end of the second arm so as to be opposed to the first jaw means such that upon pivoting of the ends of the arms toward one another the jaw means move toward one another in a straight-line fashion to effect the removal of a convertible buccal tube cap through at least one of the jaw means entering an end of the convertible buccal tube so as to effect an upward shearing force on the cap of the convertible buccal tube without imposing potentially damaging forces on the tooth that the convertible buccal tube is mounted on.

5. An orthodontic plier apparatus according to claim 4 wherein at least one of the jaw means has a removably attached tip that can be replaced when worn.

6. An orthodontic plier apparatus according to claim 4 also comprising a setscrew means for adjusting the extent to which a cap is removed upon movement of the jaw means toward one another.

7. An orthodontic plier apparatus according to claim 4 also comprising a cap retention means for retaining a removed cap with the plier for removal from a patient's mouth.

8. A method for removing a convertible buccal tube cap comprising the steps of:
   bracing one end of the convertible buccal tube independently of the tooth that the convertible buccal tube is mounted on;
   inserting a prying tip into the opening at the other end of the convertible buccal tube; and
   moving the prying tip toward the braced end of the convertible buccal tube so as to effect an upward shearing force on the cap of the convertible buccal tube.

9. A method according to claim 8 also comprising the step of retaining the removed cap for removal from a patient's mouth.

10. An apparatus for removing a convertible buccal tube cap comprising:
    means for bracing one end of the convertible buccal tube;
    means for inserting a prying tip having a remote point and a thickness that increases away from the remote point, into the opening at the other end of the convertible buccal tube; and
    means for moving the prying tip toward the braced end of the convertible buccal tube so as to effect an upward shearing force on the cap of the convertible buccal tube.

11. An apparatus according to claim 10 also comprising means for adjusting the extent to which a cap is removed upon movement of the prying tip toward the braced end.

12. An apparatus according to claim 10 also comprising means for retaining a removed cap with the apparatus for removal from a patient's mouth.

* * * * *

UNITED STATES PATENT AND TRADEMARK OFFICE
CERTIFICATE OF CORRECTION

PATENT NO. : 4,669,979
DATED : June 2, 1987
INVENTOR(S) : Wilford A. Snead

It is certified that error appears in the above—identified patent and that said Letters Patent is hereby corrected as shown below:

IN THE CLAIMS

Column 7, line 60    After comprising add -- : --.

Column 8, line 2    Change "pivtally" to --pivotally--.

Column 8, between
lines 3 and 4 insert:    --a first jaw means operatively connected to one end of the first arm; and--

Signed and Sealed this

First Day of March, 1988

Attest:

DONALD J. QUIGG

*Attesting Officer*    *Commissioner of Patents and Trademarks*